United States Patent
Ortuno et al.

[11] Patent Number: 6,051,025
[45] Date of Patent: Apr. 18, 2000

[54] FLEXIBLE INTRAOCULAR IMPLANT AND SET OF SUCH IMPLANTS

[75] Inventors: Angel Ortuno, Choisy; Dominique Durand, Annecy; Gilles Bos, La Balme de Sillingy, all of France

[73] Assignee: Corneal Laboratoires, Paris, France

[21] Appl. No.: 09/142,685

[22] PCT Filed: Mar. 13, 1997

[86] PCT No.: PCT/FR97/00445

§ 371 Date: Sep. 11, 1998

§ 102(e) Date: Sep. 11, 1998

[87] PCT Pub. No.: WO97/33536

PCT Pub. Date: Sep. 18, 1997

[30] Foreign Application Priority Data

Mar. 14, 1996 [FR] France ................................. 96 03215

[51] Int. Cl.$^7$ ........................................................ A61F 2/14
[52] U.S. Cl. ..................................................................... 623/6
[58] Field of Search ................................................ 623/6, 4

[56] References Cited

U.S. PATENT DOCUMENTS

| | | |
|---|---|---|
| 4,661,108 | 4/1987 | Grendahl et al. |
| 4,878,912 | 11/1989 | Castleman ................................ 623/6 |
| 5,019,098 | 5/1991 | Mercier ..................................... 623/6 |
| 5,047,051 | 9/1991 | Cumming. |
| 5,089,024 | 2/1992 | Christie et al. .......................... 623/6 |
| 5,139,519 | 8/1992 | Kalb ........................................ 623/6 |
| 5,192,318 | 3/1993 | Schneider et al. ...................... 623/6 |
| 5,201,763 | 4/1993 | Brady et al. ............................. 623/6 |
| 5,203,789 | 4/1993 | McDonald. |
| 5,207,708 | 5/1993 | Blumenthal ............................. 623/6 |
| 5,217,489 | 6/1993 | Van Noy et al. ........................ 623/6 |

FOREIGN PATENT DOCUMENTS

WO95/07059  3/1995  WIPO.

Primary Examiner—Jeffrey A. Smith
Assistant Examiner—Eduardo C. Robert
Attorney, Agent, or Firm—Wolf, Greenfield & Sacks, P.C.

[57] ABSTRACT

The invention relates to an intraocular implant made of a flexible material presenting an optical refractive index included between 1.40 and 1.56 including an optic portion (10) and a haptic portion, the optic portion generally being circular. The optic portion of the implant has a cylindrical circumferential surface (16) with a width e of 0.1–0.3 mm and a diameter De of 5–7 mm, and two main surfaces (12, 14), each consisting of a spherical cap (18) of which the geometrical axis coincides with the optical axis and a frusto-conical surface (20) with an inner edge connected to the edge of the spherical cap via a toroidal surface portion (22), and an outer edge connected to said circumferential surface, the thickness E of said optic portion being between 1 and 1.5 mm along the optical axis.

23 Claims, 2 Drawing Sheets

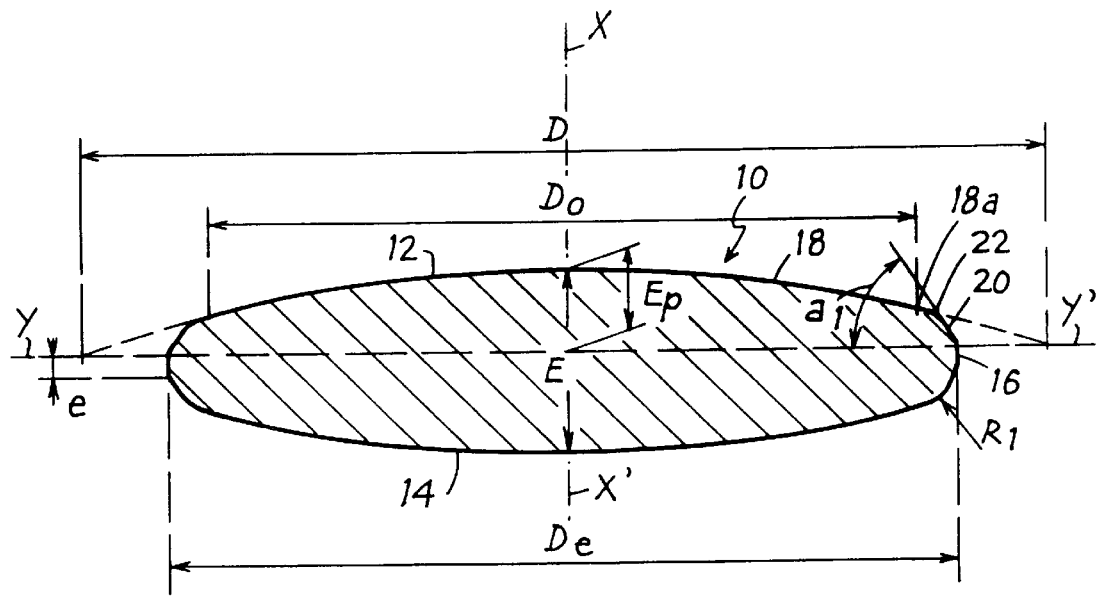
FIG_1
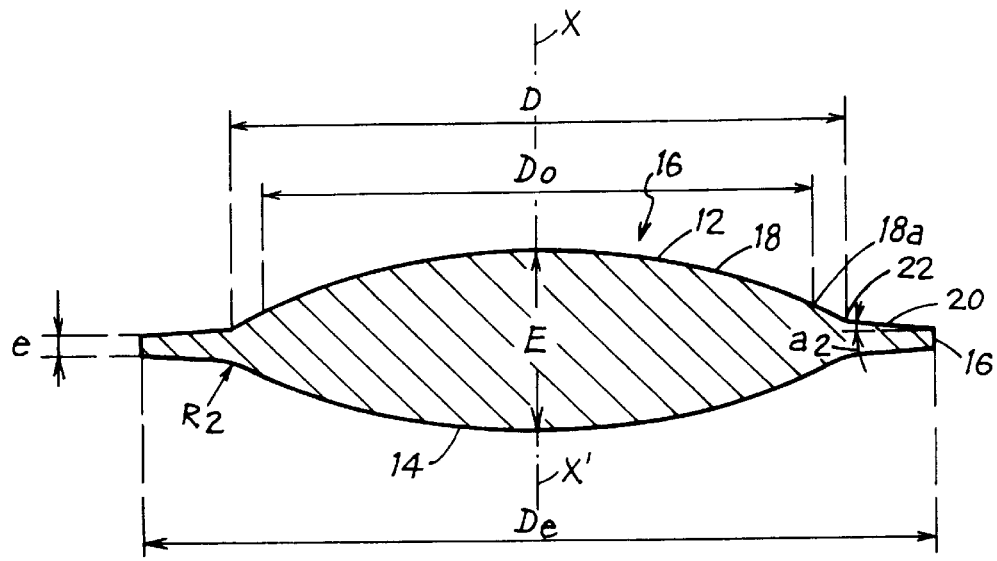
FIG_2

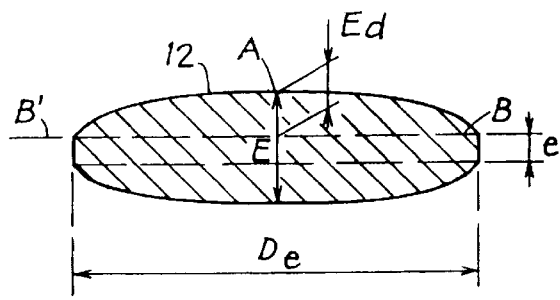
FIG_3
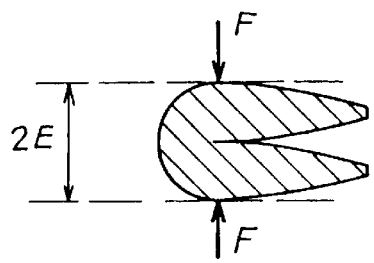
FIG_4
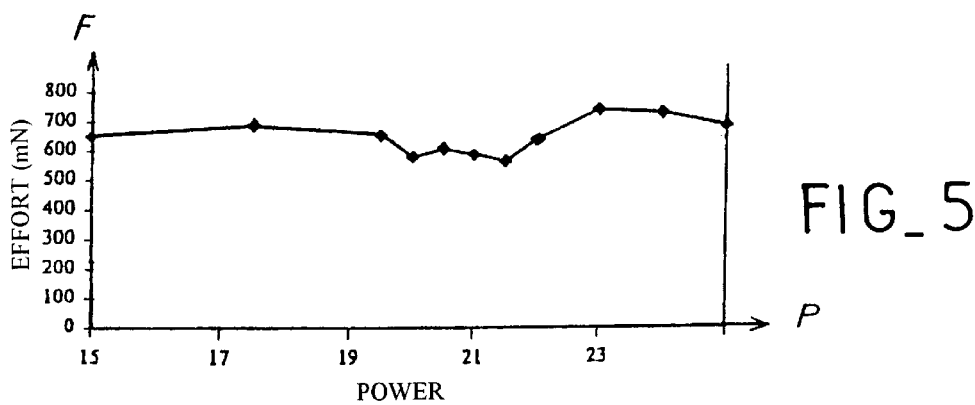
FIG_5
| EFFORT TO MAINTAIN THE IMPLANT AT 2*E | |
|---|---|
| POWER | EFFORT (mN) |
| 15 | 647 |
| 17.5 | 682 |
| 19.5 | 647 |
| 20 | 573 |
| 20.5 | 600 |
| 21 | 583 |
| 21.5 | 560 |
| 22 | 637 |
| 23 | 735 |
| 24 | 725 |
| 25 | 680 |
FIG_6

FLEXIBLE INTRAOCULAR IMPLANT AND SET OF SUCH IMPLANTS

FIELD OF THE INVENTION

The present invention has for its object a flexible intraocular implant and a set of such intraocular implants presenting optical powers extending from 10 to 30 diopters.

BACKGROUND OF THE INVENTION

The production of flexible intraocular implants, whether for the anterior chamber or for the posterior chamber of the eye, raises a certain number of problems in order to facilitate convenient positioning of the implant inside the eye by the surgeon.

The interest of these flexible implants which are, in known manner, made either of hydrogel or of silicone gel, is that the optic portion of the implant may be bent about an axis orthogonal to the optical axis at the moment of being inserted inside the eye. It will be readily understood that such bending makes it possible to reduce the "overall dimensions" of the intraocular implant and therefore to reduce the size of the incision which must be made for positioning the implant in the eye. Traditionally, the desirable size of the incision made is at present 4 mm. This size is connected with that of the incision which must be made when it is desired to extract the lens typically by phakoemulsification. It is therefore necessary that the geometrical characteristics of the implant be such that, after being bent into two about an axis orthogonal to the optical axis, the optic portion may effectively pass through this incision of 4 mm.

Three types of problem arise in the definition of the geometry of the optic portion of the implant:

firstly, it is necessary that the maximum thickness of the implant, i.e. along its optical axis, be not too great in order effectively to allow the optic portion to bend and said optic portion to be maintained in bent position, with the aid of the surgical instruments usually used for this operation;

it is also necessary that all the widthwise dimensions of the implant be sufficient for the optic portion to conserve its shape despite the stresses which may be applied thereto, particularly by the haptic portion of the implant, when the implant is positioned in the eye;

finally, it is very important, for the precision of the positioning of the implant in the eye and for the comfort of the surgeon who is carrying out this operation, that the force necessary for maintaining the optic portion of the implant in this bent position, be substantially constant for a series of implants, whatever the optical power of this implant. Conventionally, the power of the implants usually positioned ranges from 10 to 30 diopters and, more commonly still, from 15 to 25 diopters.

Nevertheless, as in any implant, the surface of the correcting portion must be sufficient to avoid the parasitic phenomena, particularly in the case of slight displacement of the implant in the eye.

It should be recalled that the optical power of the implant is defined by the radii of curvature of the anterior and posterior diopters of the implant. It will be understood that the values of these radii of curvature, which participate largely in the definition of the widthwise dimensions of the implant, are overall imposed by the optical power which it is desired to produce with the aid of the implant, it being understood that the ratio between the radii of curvature of the anterior and posterior diopters of the implant may be played on.

SUMMARY OF THE INVENTION

A first object of the invention is to provide an intraocular implant whose geometry is defined so that it can be easily bent and maintained in this bent position with a suitable holding force for the surgeon while allowing it to be inserted in the eye through an incision whose length is of the order of 4 mm, while ensuring a sufficient correcting surface.

In order to attain this object, the intraocular implant is made of a flexible material presenting an optical refractive index included between 1.40 and 1.56, including an optic portion and a haptic portion, the optic portion generally being circular, characterized in that said optic portion has a cylindrical circumferential surface with a width e of 0.1–0.3 mm and a diameter De of 5–7 mm, and two main surfaces, each consisting of a spherical cap of which the geometrical axis coincides with the optical axis and a frusto-conical surface with an inner edge connected to the edge of the spherical cap via a toroidal surface portion, and an outer edge connected to said circumferential surface, the thickness E of said optic portion being between 1 and 1.5 mm along the optical axis.

It will be understood that, by giving to each main surface, respectively anterior and posterior, of the optic portion of the implant, the specific shape defined hereinabove and by selecting the corresponding dimensions within the ranges given, easily bendable implants are effectively obtained, for a power range of from 10 diopters to 30 diopters, which may be introduced in the eye through an incision of 4 mm.

Preferably again, the diameter of the circumferential surface of the spherical cap is at least equal to 4.5 mm and preferably at least equal to 5 mm, which ensures a vision-correcting surface sufficient for the wearer of the implant.

Preferably still, the intraocular implant is characterized in that its optic portion verifies the following relationship:

$$90 < \frac{F}{n \cdot E^3} < 150$$

in which F(mN) is the force to maintain said optic portion bent in two around an axis orthogonal to the optical axis, n(MPa) is the Young's modulus of the flexible material constituting the optic portion, and E(mm) the width of the optics along the optical axis thereof.

Thanks to this characteristic of the invention, the force necessary for maintaining the optic portion of the implant bent is maintained in a relatively reduced range, for a given maximum thickness of the optic portion, this very substantially increasing the comfort of the surgeon when positioning the implant inside the eye.

The invention also relates to a set of intraocular implants each presenting an optical power included between 10 and 30 diopters and preferably between 15 and 25 diopters which all have the same geometrical characteristics, concerning the maximum thickness of the implant, the width of its circumferential wall and the outer diameter of the optic portion. These arrangements make it easier for the surgeon to position the implant and, by the choice of these numerical values within the given ranges, the surgeon can choose the set of implants corresponding to the different powers, which suits him best.

BRIEF DESCRIPTION OF THE DRAWINGS

Other characteristics and advantages of the invention will appear more readily on reading the following description of several embodiments of the invention given by way of non-limiting examples.

The description refers to the accompanying Figures in which:

FIG. 1 is a view in vertical section of the optic portion of a first type of implant according to the invention.

FIG. 2 is a view in vertical section of the optic portion of a second type of implant according to the invention.

FIG. 3 is a schematic view in vertical section of the optic portion of the implant.

FIG. 4 is a simplified view in vertical section illustrating the definition of the force of maintaining the implant bent.

FIG. 5 is a curve which represents the force F of maintenance, as a function of the power of the implant for a given family of implants; and FIG. 6 is a Table giving the force of maintenance as a function of the optical power of the implant.

DETAILED DESCRIPTION

As has already been indicated, the object of the invention is to provide flexible implants in the range of optical powers going from 10 to 30 diopters and preferably from 15 to 25 diopters, of which the particular definition, particularly the main anterior and posterior faces of the implant, makes it possible to obtain implants which are easily bendable while conserving a sufficient mechanical resistance once implanted and which, moreover, remain in a range which is relatively limited as to the value of the force which must be applied thereto to maintain them in bent position about an axis orthogonal to the optical axis, as shown in FIG. 4.

At the present time, flexible implants are produced with materials of the Hydrogel type or of the silicone gel type although other materials which can be used exist. The optical refractive index of these materials may vary from 1.4 to 1.56 depending on their composition and the additives which may be incorporated therein. More frequently, this index is included between 1.41 and 1.51. It will be understood that, for a given implant power, this index will, of course, influence the radii of curvature of the anterior and posterior diopters of the implant.

Referring now to FIGS. 1 and 2, a preferred embodiment of the intraocular implant will now be described. The optic portion 10 is limited by a main anterior face 12, a main posterior face 14 and a cylindrical circumferential surface 16. The anterior face 12, like the posterior face 14, is constituted by a spherical cap portion 18 of axis XX', and by a frusto-conical surface 20 likewise of axis XX'. The edge 18a of the spherical cap 18 is connected to the frusto-conical surface 20 by a toroidal surface portion 22 of axis XX', and of radius R1. R will designate the radius of the spherical cap.

In FIG. 1, De designates the diameter of the cylindrical circumferential surface and e its width or height. In this same Figure, E designates the maximum thickness of the optic portion along its geometrical axis XX'. Do represents the diameter of the edge 18a of the spherical cap and D represents the "natural" diameter of the diopters constituting the optically correcting portion of the main faces of the implant. The "natural" diameter D is the diameter of the circle corresponding to the intersection of the spherical cap with plane BB' of FIG. 3, i.e. the plane which contains the upper limit of the circumferential surface 16. Finally, $a_1$ is the angle that the frusto-conical surface 20 makes, in an axial plane of section, with plane YY' of the optic portion.

In FIG. 1, the main anterior (12) and posterior (14) faces are identical. However, it goes without saying that the two faces might be different, particularly concerning the radius of curvature of the spherical caps.

According to the invention, the maximum thickness E of the implant is included between 1.0 and 1.5 mm, the width e of the circumferential surface 16 of the optic portion is included between 0.1 and 0.3 mm, and the outer diameter De of the optic portion is included between 5 and 7 mm. These ranges of values ensure that the optic portion is suitably bendable while presenting a sufficient mechanical resistance to maintain the shape of the optic portion when the implant is in the eye. In addition, these dimensions allow the bent implant to be introduced into the eye through an incision of the order of 4 mm. It should be added that, in order to ensure a sufficient surface for the optically active portion constituted by the spherical caps 12, the diameter Do is at least equal to 4.5 mm and, preferably, larger than 5 mm.

It will be understood that, if particular values are fixed for E, e, and De, depending on the value of the radius of curvature of the spherical cap, the "natural" diameter D of the diopter is greater or less than the outer diameter De of the optic portion.

Referring now to FIG. 3, the parameter Ed represents the distance between the apex A of the spherical cap and the plane BB' upwardly limiting the cylindrical portion of the optic portion. It will be designated the camber of the spherical cap. It will be understood that there are two situations, depending on whether the natural diameter D is greater than De (FIG. 1) or less than De (FIG. 2), the limit corresponding to the case where D=De.

It may be established that, for this limiting value, the radius of curvature R of the spherical cap is given by the relationship:

$$R = \frac{De^2 + 4Ed^2}{8Ed},$$

therefore, if $$R > \frac{4Ed^2 + De^2}{8Ed},$$

the "natural" diameter of the diopter is greater than De and one is in the configuration of FIG. 1. In the contrary case, one is in the configuration of FIG. 2.

In order to remain within the framework fixed by the invention, it will be understood that, in the case of FIG. 1, the frusto-conical surface 20 intersects the spherical cap 18. On the contrary, in the case of FIG. 2, the frusto-conical surface 20 laterally extends the spherical cap 12.

In the case of the configuration of FIG. 1, the angle $a_1$ must be included between 90 degrees and 6 degrees. In the case of FIG. 2, the angle $a_2$ must be included between 0 and 40 degrees.

In addition, the radii $R_1$ and $R_2$ of the toroidal surface portion are constant and preferably included between 0.1 and 1 mm.

It will be understood that, for given values of De, Ed and R, the choice of the angles $a_1$ or $d_2$ determines the diameter Do of the edge of the spherical cap, i.e. the useful optical correction surface.

The determination of the values of angles $a_1$ and $a_2$ in the given ranges results from a compromise between two objectives to be attained.

On the one hand, it is desirable that Do be as large as possible, which incites one to choose a low value for $a_2$ and a value for $a_1$ which is as large as possible. On the other hand, the optic portion of the implant must have a sufficient mechanical resistance, which leads to avoiding having an edge of the optic portion which is too thin, which leads one to choose a relatively high value for $a_1$ and $a_2$.

As has already been indicated, another very important characteristic of the optic portion is connected with the effort necessary to maintain it bent. This value of the effort is important for the surgeon's comfort and for the safety of the operation. In addition, it is desirable that this effort of bending be substantially constant whatever the power of the implant.

Tests made have shown that, to that end, it was desirable to have the relationship:

$$90 < \frac{F}{n \cdot E^3} < 150$$

expression in which E is the maximum thickness of the implant, n the Young's modulus of the material used and F the force for maintaining the optic portion in bent form.

FIG. 5 illustrates what bending of the optic portion about an axis orthogonal to the optical axis is intended to mean. The force F must be sufficient to maintain the implant between two planes separated by a width equal to twice the thickness E. However, it appears that this force must not be greater than 900 mN. In effect, beyond this limit, by reaction, the implant risks being ejected from the surgical instrument which maintains it bent.

It should be added that the materials used present Young moduli which are included between 3.7 MPa and 4.46 MPa.

It will be understood that, in view of the above formula, it is possible, for a chosen bending force and for a given Young's modulus, to determine the maximum thickness E of the optic portion, this width being included within the range mentioned above.

The value of Ed for the two main faces is deduced from the value of E and the choice of the radii of curvature of the spherical caps corresponding to the optical power of the implant to be made. The value of the diameter De having been defined, it can be determined whether the optic portion corresponds to the configuration of FIG. 1 or of FIG. 2. Depending on the criteria set forth hereinabove, angle $a_1$ or angle $a_2$ will then be defined.

FIGS. 5 and 6 illustrate the force of bending F as a function of the optical power P for a family of intraocular implants for which the thickness E is equal to 1.1 mm and the optical diameter is equal to 5.75 mm.

We claim:

1. An intraocular lens having an optical portion formed of a flexible, light transmitting material and an optical axis, said optical portion having a thickness along said optical axis between about 1.0 and 1.5 mm and comprising:
    an anterior main surface formed of a generally spherical cap and having a generally circular edge;
    a posterior main surface spaced from said anterior main surface along said optical axis, said posterior main surface being formed of a generally spherical cap and having a generally circular edge;
    a lateral surface disposed between said anterior main surface and said posterior main surface and having a generally cylindrical shape and an axis generally coincident with said optical axis, said lateral surface having an anterior edge and a posterior edge;
    a first anterior connecting surface having an inner edge and an outer edge and being formed as a portion of a toroidal surface, said first anterior connecting surface being generally symmetrically disposed about said optical axis, the inner edge of said first anterior connecting surface being connected to the edge of said anterior main surface;
    a second anterior connecting surface connecting the outer edge of said first anterior connecting surface with the anterior edge of said lateral surface, said second anterior connecting surface comprising a frusto-conical surface and being generally symmetrically disposed about said optical axis;
    a first posterior connecting surface having an inner edge and an outer edge and being formed as a portion of a toroidal surface, said first posterior connecting surface being generally symmetrically disposed about said optical axis, the inner edge of said first posterior connecting surface being connected to the edge of said posterior main surface; and
    a second posterior connecting surface connecting the outer edge of said first posterior connecting surface with the posterior edge of said lateral surface, said second posterior connecting surface comprising a frusto-conical surface, and being generally symmetrically disposed about said optical axis.

2. The intraocular lens according to claim 1 wherein a diameter of the edge of each of said anterior and posterior main surfaces is at least about 4.5 mm.

3. The intraocular lens according to claim 1 wherein said optical portion is constructed to be bent around an axis orthogonal to said optical axis and maintained in a bent state by application of a force (F), wherein said flexible material of said optical portion has a Young's modulus (n) and a thickness (E) along the optical axis and wherein $$90 < \frac{F}{nE^3} < 150.$$

4. The intraocular lens according to claim 3 wherein at least one of said second anterior and posterior connecting surfaces forms an angle with a plane perpendicular to said optical axis, wherein said angle is between 90 degrees and 9 degrees if $$R > \frac{4Ed^2 + De^2}{8Ed}$$

wherein (R) is a radius of an associated one of said anterior and posterior main surfaces measured from said optical axis, (Ed) is a distance between an apex of said associated one of said anterior and posterior main surfaces and a plane containing a respective edge of said associated one of said anterior and posterior main surfaces and (De) is a diameter of said lateral surface.

5. The intraocular lens according to claim 4, wherein said angle is between 0 and 40 degrees if $$R < \frac{4Ed^2 + De^2}{8Ed}$$

6. The intraocular lens according to claim 1 wherein at least one of said second anterior and posterior connecting surfaces forms an angle with a plane perpendicular to said optical axis, wherein said angle is between 90 degrees and 9 degrees if $$R > \frac{4Ed^2 + De^2}{8Ed}$$

wherein (R) is a radius of an associated one of said anterior and posterior main surfaces measured from said optical axis, (Ed) is a distance between an apex of said associated one of said anterior and posterior main surfaces and a plane containing a respective edge of said associated one of said anterior and posterior main surfaces and (De) is a diameter of said lateral surface.

7. The intraocular lens according to claim 6 wherein said angle is between 0 and 40 degrees if $$R < \frac{4Ed^2 + De^2}{8Ed}$$

8. The intraocular lens according to claim 1 wherein said first anterior and posterior connecting surfaces each have a radius between 0.1 and 1 mm.

9. The intraocular lens according to claim 1 wherein a diameter of said edge of each of said anterior and posterior main surfaces is at least equal to 5 mm.

10. A set of intraocular lenses, each intraocular lens having an optical portion as recited in claim 1, an optical power between 10 and 30 diopters, and a same thickness along said optical axis.

11. The intraocular lens according to claim 1 wherein said flexible material of said optical portion has a refractive index between about 1.40 and 1.56.

12. The intraocular lens according to claim 1 wherein said lateral surface has a diameter between about 5 and 7 mm and a width measured in a direction parallel to said optical axis between about 0.1 and 0.3 mm.

13. The intraocular lens according to claim 1, wherein said posterior and anterior main surfaces are symmetrically disposed about said optical axis.

14. An intraocular implant having an optical portion formed of a flexible material having an optical refractive index between 1.40 and 1.56 and being generally circular in cross-section, said optical portion having an optical axis and a thickness along said optical axis between about 1.0 and 1.5 mm, said optical portion comprising:
    a cylindrical, circumferential surface having a width measured parallel to said optical axis of 0.1–0.3 mm and a diameter of between 5 and 7 mm;
    two main surfaces, each main surface including a spherical cap having a geometric axis coincident with said optical axis and an edge having a diameter, the diameter of the edge of each said spherical cap being at least equal to 4.5 mm; and
    two frusto-conical surfaces, each surface having an inner edge connected to a corresponding edge of a corresponding one of said spherical caps by a toroidal surface portion and an outer edge connected to said circumferential surface.

15. A set of intraocular implants, each implant having an optical portion as defined in claim 14, an optical power between 10 and 30 diopters, and a same thickness along said optical axis.

16. The intraocular implant according to claim 14 wherein at least one of said main surfaces of said optical portion satisfies the following relationship when an angle formed between a frusto-conical surface associated with said one of said main surfaces and a plane perpendicular to said optical axis is between 90 degrees and 6 degrees:

$$R > \frac{4Ed^2 + De^2}{8Ed}$$

wherein (R) is a radius of said one of said main surfaces of said optical portion as measured from said optical axis, (De) is said diameter of said circumferential surface, and (Ed) is a camber of said one of said main surfaces.

17. The intraocular implant according to claim 16 wherein the following relationship is satisfied:

$$R < \frac{4Ed^2 + De^2}{8Ed}$$

when said angle between said frusto-conical surface associated with said one of said main surfaces and said plane perpendicular to said optical axis is between 0 and 40 degrees.

18. The intraocular implant according to claim 14, wherein said flexible material has a Young's modulus (n) and wherein said optical portion can be bent around an axis orthogonal to said optical axis and maintained in a bent state by application of a force (F) to said optical portion, said force (F), said Young's modulus (n) and said thickness (E) of said optical portion satisfying the following relationship:

$$90 < \frac{F}{nE^3} < 150.$$

19. The intraocular implant according to claim 18 wherein at least one of said main surfaces of said optical portion satisfies the following relationship when an angle formed between a frusto-conical surface associated with said one of said main surfaces and a plane perpendicular to said optical axis is between 90 degrees and 6 degrees:

$$R > \frac{4Ed^2 + De^2}{8Ed}$$

wherein (R) is a radius of said one of said main surfaces of said optical portion as measured from said optical axis, (De) is said diameter of said circumferential surface, and (Ed) is a camber of said one of said main surfaces.

20. The intraocular implant according to claim 19 wherein the following relationship is satisfied:

$$R < \frac{4Ed^2 + De^2}{8Ed}$$

when said angle between said frusto-conical surface associated with said one of said main surfaces and said plane perpendicular to said optical axis is between 0 and 40 degrees.

21. An intraocular implant having an optical portion formed of a flexible material, said optical portion having an optical axis and a thickness along said optical axis between about 1.0 and 1.5 mm, said optical portion comprising:
    a cylindrical, circumferential surface having a width measured parallel to said optical axis and a diameter;
    two main surfaces, each main surface including a spherical cap having a geometric axis coincident with said optical axis and an edge having a diameter;
    two frusto-conical surfaces, each surface having an inner edge connected to a corresponding edge of a corresponding one of said spherical caps by a toroidal surface portion and an outer edge connected to said circumferential surface;

wherein said optical portion can be bent around an axis orthogonal to said optical axis and maintained in a bent state by application of a force (F) to said optical portion, said force (F), a Young's modulus (n) of said flexible material and a thickness (E) of said optical portion satisfying the following relationship:

$$90 < \frac{F}{nE^3} < 150.$$

22. An intraocular implant having an optical portion formed of a flexible material, said optical portion having an optical axis and a thickness along said optical axis between about 1.0 and 1.5 mm, said optical portion comprising:

a cylindrical, circumferential surface having a width measured parallel to said optical axis and a diameter;

two main surfaces, each main surface including a spherical cap having a geometric axis coincident with said optical axis and an edge having a diameter;

two frusto-conical surfaces, each surface having an inner edge connected to a corresponding edge of a corresponding one of said spherical caps by a toroidal surface portion and an outer edge connected to said circumferential surface;

wherein at least one of said main surfaces of said optical portion satisfies the following relationship when an angle formed between a frusto-conical surface associated with said one of said main surfaces and a plane perpendicular to said optical axis is between 90 degrees and 6 degrees:

$$R < \frac{4Ed^2 + De^2}{8Ed}$$

wherein (R) is a radius of said one of said main surfaces of said optical portion as measured from said optical axis, (De) is said diameter of said circumferential surface, and (Ed) is a camber of said one of said main surfaces.

23. An intraocular implant having an optical portion formed of a flexible material, said optical portion having an optical axis and a thickness along said optical axis between about 1.0 and 1.5 mm, said optical portion comprising:

a cylindrical, circumferential surface having a width measured parallel to said optical axis and a diameter;

two main surfaces, each main surface including a spherical cap having a geometric axis coincident with said optical axis and an edge having a diameter;

two frusto-conical surfaces, each surface having an inner edge connected to a corresponding edge of a corresponding one of said spherical caps by a toroidal surface portion and an outer edge connected to said circumferential surface;

wherein at least one of said main surfaces of said optical portion satisfies the following relationship when an angle formed between a frusto-conical surface associated with said one of said main surfaces and a plane perpendicular to said optical axis is between 0 degrees and 40 degrees:

$$R > \frac{4Ed^2 + De^2}{8Ed}$$

wherein (R) is a radius of said one of said main surfaces of said optical portion as measured from said optical axis, (De) is said diameter of said circumferential surface, and (Ed) is a camber of said one of said main surfaces.

* * * * *